United States Patent [19]

Flores-Cotera et al.

[11] Patent Number: 5,593,890
[45] Date of Patent: Jan. 14, 1997

[54] APPARATUS SUITABLE FOR CONDUCTING GAS-LIQUID REACTIONS

[75] Inventors: Luis B. Flores-Cotera; Sergio García-Salas, both of Mexico City, Mexico

[73] Assignee: Centro de Investigación y de Estudios Avanzados del Instituto Politécnico Nacional, Mexico City, Mexico

[21] Appl. No.: 429,687

[22] Filed: Apr. 27, 1995

Related U.S. Application Data

[62] Division of Ser. No. 963,980, Oct. 23, 1992, Pat. No. 5,426,024.

[51] Int. Cl.$^6$ .............................. C12M 1/21; C12M 1/36
[52] U.S. Cl. ..................... 435/286.5; 435/286.6; 435/295.1; 435/295.2; 435/301.1; 96/157; 96/174; 96/176
[58] Field of Search ................... 435/286.1, 286.5, 435/286.6, 289.1, 295.1, 295.2, 301.1, 246, 812; 95/1, 19, 24, 22, 154, 155, 23, 157, 341, 242; 96/155, 156, 157, 168, 169, 172, 174, 176; 261/121.1, 122.1, 126, DIG. 19

[56] References Cited

U.S. PATENT DOCUMENTS

| | | | |
|---|---|---|---|
| 3,563,858 | 2/1971 | Worthington et al. | 195/107 |
| 3,586,605 | 6/1971 | Hosler | 195/28 |
| 3,672,953 | 6/1972 | Coty et al. | 435/301.1 |
| 3,739,795 | 6/1973 | Hyde et al. | 55/178 |
| 3,806,423 | 4/1974 | Karrenbauer et al. | 195/109 |
| 3,857,757 | 12/1974 | Herrick et al. | 195/109 |
| 3,910,826 | 10/1975 | Kataoka | 195/142 |
| 3,926,737 | 12/1975 | Wilson et al. | 195/108 |
| 4,003,724 | 1/1977 | Payne et al. | 55/87 |
| 4,169,010 | 9/1979 | Marwil | 435/247 |
| 4,263,143 | 4/1981 | Ebner et al. | 435/301.1 |
| 4,325,923 | 4/1982 | Botton et al. | 423/234 |
| 4,373,024 | 2/1983 | Hunt | 435/41 |
| 4,414,329 | 11/1983 | Wegner | 435/68 |
| 4,545,945 | 10/1985 | Prave et al. | 435/295.2 |
| 4,624,745 | 11/1986 | Sande et al. | 96/176 |
| 4,670,397 | 6/1987 | Wegner et al. | 435/289 |
| 4,752,564 | 6/1988 | Hopkins | 435/3 |
| 4,883,759 | 11/1989 | Hopkins | 435/289 |
| 4,987,082 | 1/1991 | Gallagher | 435/289 |
| 5,426,024 | 6/1995 | Flores-Cotera et al. | 435/812 |

FOREIGN PATENT DOCUMENTS 2172818  9/1986  United Kingdom .

OTHER PUBLICATIONS

Prins, et al., Trends in Biotechnol., vol. 5, Nov. (1987).
van't Riet et al., "Foam", Basic Bioreactor Design, Marcel Dekker, Inc., 1991, pp. 274–291.
Blenke, "Biochemical Loop Reactors", Biotechnology vol. 2., H. J. Rehm and G. Reed Eds., VCH Verlagsgesellschaft, Weinheim, 1985 465–517.

*Primary Examiner*—William Beisner
*Attorney, Agent, or Firm*—Jacobson, Price, Holman & Stern, PLLC

[57] ABSTRACT

An improved apparatus for conducting gas-liquid reactions, comprising a vessel having at least one ascending flow chamber and at least one descending flow chamber. The vessel is especially useful in conducting high cell density fermentation processes, for maintaining a predetermined and relatively high gas holdup within the vessel and simultaneously preventing foaming through hydrodynamics.

6 Claims, 2 Drawing Sheets

APPARATUS SUITABLE FOR CONDUCTING GAS-LIQUID REACTIONS

This is a divisional of application Ser. No. 07/963,980 filed Oct. 23, 1991, now U.S. Pat. No. 5,426,024.

The invention relates to a fermentation method and to an improved fermentor, for growing microorganisms and/or to produce metabolites from microorganisms, especially at high cell densities. Particularly, our fermentation method and fermentor is suitable for conducting aerobic fermentation processes under controlled and relatively high gas holdup conditions within the fermentor.

BACKGROUND OF THE INVENTION

Up to the present time, fermentations requiring a high rate of oxygen input, such as high cell density fermentation processes disclosed in U.S. Pat. No. 4,414,329 by Wegner (assigned to Phillips Petroleum Co.), have been generally conducted in fermentation vessels equipped with agitation means and mechanical defoamer means. The patent literature disclosing such fermentors includes: U.S. Pat. No. 4,670,397, U.S. Pat. No. 4,752,564, U.S. Pat. No. 4,883,759, U.S. Pat. No. 4,373,024. Agitated fermentors are difficult to adapt to supply the very high rate of oxygen input, necessary to conduct high cell density fermentation processes for large scale plants, and for various physical and biological reasons, it is not commercially feasible to increase the size of those vessels beyond certain limits. Stirrers and mechanical foam breakers employed in high cell density fermentations require very high energy input, which is both, costly and a major problem in large fermentors. Problems of drive shaft and bearing design for transmitting the enormous torque arise. In addition, seals associated with the stirrer and the foam breaker are often difficult to clean and sterilize and in many instances create cleaning and asepsis problems. Consequently, there is a continuing need for improved fermentors of even larger capacity than those built to date, and capable of conducting aerobic fermentation processes at high cell densities and high productivities. At the same time, a fermentor which does not require moving parts for effective foam control, which is simple in construction, economical to manufacture and to maintain, and which gives good results in terms of achievable oxygen transfer rate and power consumption would provide obvious advantages.

Fermentors having non mechanical agitation and/or non mechanical foam control means are a desirable alternative to mechanically agitated systems. Potential advantages are as follows: Improved maintenance of sterility because no top and bottom entering shafts, construction of larger fermentors is possible because the design is not limited by motor size and shaft length and weight, the fermentors are cheaper to fabricate since no agitator, gear box or crane rail is needed, less structural steel is used, better energy efficiency and reduced maintenance. Our invention thus is intended to provide a fermentor and a fermentation method which overcome several shortcomings of fermentors and fermentation methods of the present technology.

OBJECTS OF THE INVENTION

In one aspect, our invention relates to an improved method for aerobic propagation of suitable microbial cells. Another object of this invention is provide an improved fermentation apparatus suitable for aerobic culturing of microbial cells. Still other objects of the present invention are to provide a fermentation method and a fermentor, particularly useful for conducting high cell density fermentation processes. Yet other objects of the present invention are to provide a fermentation method and an improved fermentor which is economical, efficient, simple and reliable, for conducting high cell density fermentation processes. Further according to the invention we provide a fermentation method and a fermentor suitable to grow microbial cells and/or produce their metabolites within a fermentor, operating under controlled and relatively high gas holdup conditions. Still other objects of the invention are to provide a fermentation method and a fermentor in which foaming is prevented by non mechanical means.

The method of the present invention can be generally characterized as the aerobic fermentation of a suitable carbon source assimilable by a microorganism in a fermentor, in which a controlled and relatively high gas holdup is maintained. The gas holdup can be defined as the volume fraction of the gas phase (e.g. air) contained within a given volume of a mixture of gas and liquid phases or as the ratio of the volume of the gas phase to the sum of the volume of the gas and liquid phases. A distinction is drawn between gas holdup and foam: in gas holdup the gas bubbles that are dispersed in the liquid are more spherical and the gas/liquid volume ratio usually is lower than two; in foam the bubbles are polyhedral, forming a honeycomb structure and the gas/liquid ratio is larger than two and usually larger than three. Still a simpler practical distinction can be made; gas holdup is the volume fraction of gas in the gassed broth and foam is a layer of bubbles on top of the fermentation broth. The method of our invention can be applied to control and to maintain a relatively high gas holdup in the gas/liquid mixture contained within the fermentor, particularly in those fermentation processes where by nature of the microbial growth process, materials which have surfactant properties are released from microorganisms to the medium and thus induce foaming. Especially, fermentations which demand very high oxygen transfer rates for microbial cell growth or cell metabolites production, in an aqueous medium containing a carbon source can be enhanced by our invention.

SUMMARY OF THE INVENTION

Aerobic microbial conversions are oxidation reactions which demand large quantities of molecular oxygen. Hence, one of the main factors limiting cells generation rate and the productivity in an aerobic fermentor, is the oxygen transfer rate (OTR). The oxygen transfer rate is primarily a function of bubble surface area, consequently, the oxygen containing gas is preferably introduced to the fermentor in a fine bubble form, in order to provide a large contact surface area between the gas and liquid phases. Nevertheless, fine gas bubbles dispersed in a pure liquid, for instance water, tend to join to form larger ones. So, even with the finest primary dispersion and depending on the degree of turbulence in the space in question, bubble sizes between about 2 to 5 mm are formed after leaving the sparging zone. This process, known as bubble coalescence, is caused by the fact that the liquid film between two adjacent gas bubbles becomes thinner and thinner until it eventually ruptures. On the other hand, many fermentation broths contain extracellular materials which have surfactant properties. In these cases, coalescence is naturally suppressed with elapsed fermentation time, as these surfactant materials released from microorganisms accumulate in the fermentor. As a result, fermentation broths have a tendency of foaming and gas holdup generally increases with time. Foam is largely a result of stabilization of the liquid films by proteins, and it has a number of consequences. A foaming broth can have better oxygen transfer characteristics, by a factor of two or more, than a similar broth containing an antifoam agent. Since this increases productivity and reduces considerably the power consumption for mass transfer, this effect is advantageous. However, excessive foaming is also a common problem in many fermentation processes. Foaming results in inefficient use of fermentor volume and in a heterogeneous fluid with the bulk of cells trapped in the foam. Overflow may occur and exit filters may be wetted resulting in an increasing contamination risk. In actual practice, foaming is generally reduced by sudden antifoam additions in response to the level of the foam layer. However, this also reduces considerably the gas holdup and the oxygen tranfer rate, because the collapse of bubbles in the foam also favors the coalescence of bubbles within the broth, resulting in larger bubbles with reduced surface to volume ratios. Along with these effects, the sharp drop of the oxygen transfer rate produces a severe oxygen limitation, and consequently reduced yields, expressed as grams of cells/grams of substrate, and reduced productivities. Steady state conditions are lost during a continuous fermentation process because all above mentioned disturbances and the broth volume varies uncontrollably with variation in gas holdup. Considering the undesirable effects of sudden antifoam additions, it is clear that improved foam control methods are necessary to keep fermentation volume, liquid circulation rate, productivity and steady operating conditions in fermentation processes. As mentioned, conditions which cause the collapse of bubbles in the foam layer also favor the coalescence of bubbles within the broth, resulting in larger bubbles and reduced oxygen transfer rate from the gas phase to the broth. The fermentation method and fermentor of the present invention, can be suitably employed to resolve these two opposing phenomena to produce a non foaming fermentation, with high oxygen transfer characteristics while maintaining steady operating conditions. Our fermentation method and fermentor, can be suitably employed to keep a predetermined and relatively high gas holdup within the fermentor vessel, by continuously controlling the antifoam feed rate in response to the gas holdup in the gassed broth mixture contained within said fermentor vessel. Our fermentation method and fermentor also can be employed to prevent foam accumulation within the upper part of the fermentor vessel without the use of mechanical assistance, while maintaining a relatively high oxygen transfer rate. The fermentor is an improvement over fermentors known for aerobic culturing of microorganisms, preferably but not exclusively over loop fermentors which has been described by Blenke in H. J. Rehm and G. Reed (Ed.) "Biotechnology" Volume 2, chapter 21, pp. 470–479, VHC Verlagsgesellschaft, Weinheim (1985). Non stirred loop fermentors are preferred, but our invention also can be employed to enhance stirred loop fermentors and avoid costly mechanical foam breaker devices. Suitable fermentors which can be employed with our invention include but are not restricted to loop fermentors having internal guiding parts forming at least a chamber of ascending flow (riser) and at least a chamber of descending flow (downcomer), communicating with each other at their upper and lower ends to permit broth circulation in a loop pattern. An oxygen containing gas is injected into the fermentor at or near the lower end of the riser, and this serves both to aerate the broth and to cause it to circulate upwardly in the riser and downwardly in the downcomer. The oxygen containing gas may be supplied by any suitable means. Conveniently, gas is supplied to the riser through a perforated pipe having plurality of holes and located in the fermentor bottom. Said gas also can be sparged through venturi type nozzles, porous media or open ended pipes, if desired with associated downstream bubble breakers, meshes, grids, vanes or moving parts, or any combination of these techniques as known in the art. In addition to the airlift effect, any other mechanical or hydraulic means can be utilized to promote circulation.

Our fermentor is provided with gas holdup sensing means to provide a continuous output signal responsive to the gas holdup in the gassed broth mixture contained in the fermentor. The fermentor is also provided with a controller operatively related to said gas holdup sensing means, to regulate or alternately activate/deactivate antifoam addition in response to said gas holdup sensing means.

Coalescence is strongly impeded during a fermentation process by extracellular materials naturally released from microorganisms. Since smaller gas bubbles are formed and maintained, more bubbles are entrained into the downflow, and the gas holdup in the gassed broth mixture becomes larger with time. It is important that gas holdup does not exceed a certain maximum value as this adversely affect performance and fermentor volume utilization. For this reason, if the gas holdup is greater than desired, the antifoam flow rate shall be increased through the control action to cause an increased rate of bubble coalescence and by this means slowly reduce the gas holdup to desired values. If the gas holdup is lower than desired, the antifoam feeding shall be reduced or even stopped through the control action to prevent a further gas holdup fall.

Foam originates when bubbles ascending in the riser reach the free surface within the fermentor. At the moment that gas and liquid leave the bulk liquid volume, a process of drainage starts. This leads to a decrease in liquid content and to a decreased distance between the bubbles until mainly liquid films are present between them. Finally a honeycomb structure of air bubbles separated by very thin walls of liquid connected by plateau borders results from this process. This phenomena can be appreciated as whitish spots of foam in "statu nacendi" leaving the riser. While running our loop fermentors, we have observed that by maintaining a proper gassed broth level within the fermentor, a flow pattern develops such that, said foam in "statu nacendi" is effectively entrained by the circulating flow, through a vortex formed due to the flow deflection from the riser to the downcomer. Thus, if this flow pattern is sustained, the undesirable stable honeycomb structure is prevented and consequently foam accumulation in the upper part of the vessel is not possible. In addition, if the proper gassed broth level is sustained, the gas holdup and the oxygen transfer rate increases with time up to desirable values, without foam accumulation within the upper portion of the fermentor. Thus, there must be a free surface in the upper portion of the fermentor, large air bubbles rise to this free surface and air is then disengaged from the broth without the use of any mechanical means. However, if the gassed broth level is too high above the upper edge of the draft tube, for instance more than two times the diameter of the upper region of the fermentor above the upper edge of the draft tube, the vortex is absent. Instead, at least a portion of the free surface will remain relatively flat, and a foam layer will accumulate within the fermentor, even before that gas holdup increases up to desirable values. Gassed broth levels higher than two times the diameter of the fermentor head (D) above the upper edge of the draft tube, generally result in a relatively flat free surface where accumulation of a foam layer takes place, thus avoiding to take full advantage of our invention. For that reason, the gassed broth level should be preferably maintained between 0.1 to 2.0D, and more preferably between 0.5 to 0.8D above the upper edge of the draft tube. Our controlled gas holdup fermentation method can be employed with research and industrial, preferably continuous fermentors, to achieve stable operating conditions, to maintain high productivities and to minimize antifoam agent consumption. In contrast with methods employing mechanical defoamers, our fermentation method takes advantage of hydrodynamic foam suppression which requires no shaft arrangements, facilitates sterility maintenance, requires no additional energy input and is not a factor limiting scale up. The fermentation method and fermentor of our invention can be suitably used in many fermentation processes, where a carbon source is converted to cells or their metabolites, and where high oxygen solution rate in a fermentation broth is desired. Suitable sources of carbon material include any feed which can be used to make microorganisms or their metabolites, for example, glucose, sucrose, molasses, cheese whey, sugar cane bagasse, hydrocarbons and others. Such metabolites include but are not limited to amino acids, organic acids, polysaccharides, antibiotics, vitamins, enzymes, rDNA products such as interferon, growth hormones and many others.

As required, detailed embodiments of the present invention are disclosed herein, however it is to be understood that the disclosed embodiments are merely examples of the invention which may be embodied in various forms. Therefore, specific structural and functional details disclosed herein are not to be interpreted as limiting, but merely as a basis for the claims and as a basis for teaching one skilled in the art to employ the present invention in any appropriate manner. For convenience the detailed description will refer to a fermentation method and to a fermentor. It should be understood however, that the method and apparatus of the invention may be used in any other process wherein gas is injected into a liquid, the resulting mixture is circulated and in which disengagement of gas from the liquid takes place.

DETAILED DESCRIPTION OF THE INVENTION

Figure 1:
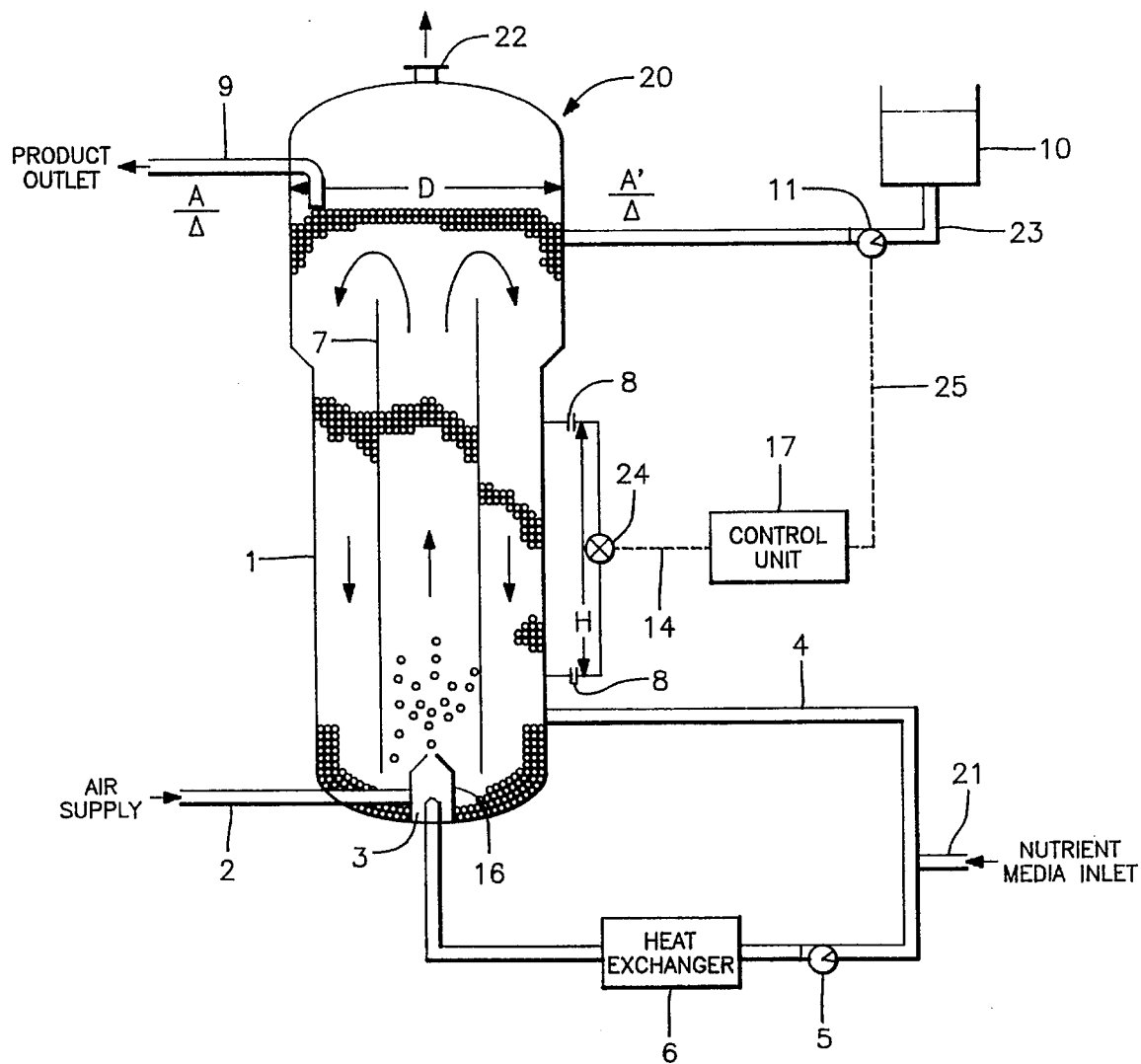
FIG. 1 is a side elevation of a fermentor illustrating one embodiment of the present invention.

FIG. 1 illustrates a fermentor generally designed by the reference character 20. The fermentor comprises a closed fermentation vessel 1 having a hollow interior. A draft tube 7 is disposed within the vessel 20 and provides a flow path for the circulating broth mixture contained within said vessel. Pipe 2, provides means for introducing a source of oxygen, such as air or air supplemented by pure oxygen into the medium. Air dispersion is accomplished by removing fermentation broth from the fermentation vessel by means of a suitable pump 5, and reinjecting the broth through one or several venturi jet mixers 3, whereby it is mixed with the air under high shear conditions, to form a dispersion of small gas bubbles into the broth. An outlet 22 communicates with the interior of the upper portion of the vessel 1 and provides means for exhausting the air from the vessel 1. The fermentor of the invention may include a heat exchanger 6, which serves as a cooler to prevent the temperature of the circulating culture from rising above the optimum temperature of growth of the microorganism in the culture. One or several inlets 21, provide means for delivery of nutrient medium containing suitable sources of carbon, nitrogen, phosphorus, potassium, magnesium, calcium, sulfur, as well as trace quantities of copper, manganese, molybdenum, zinc, iron, boron, iodide, and selenium. The relative quantities of these nutrients materials can vary in accordance with the microorganism employed or with the desired metabolite to be produced. Nutrient medium may also contain vitamins if their presence is required for microorganism growth, precursor compounds of the metabolite to be produced or required chemical compounds for biochemical conversions. If desired, also a fixed but still small amount of antifoam can be supplied through inlet 21. The vessel 1 is provided with means for direct or indirect sensing of the gas holdup in the circulating broth mixture. For instance, the vessel 1 is provided with means for sensing the differential pressure 8 between two sensing points separated by a vertical distance H and in contact both with the gassed broth mixture. The differential pressure sensed is derived from the difference between the hydrostatic pressure of the broth between the bottom and top sensors 8, and indirectly is indicative of the gas holdup in the zone between such sensors. Differential pressure (dp) measured as liquid column, given in centimeters (cm), is related to gas holdup ($\epsilon$) by equation $\epsilon=1-dp/H$, where H is given in cm. Differential pressure sensing points 8 can be located in the downcomer or riser regions, or in any other suitable region within the fermentor because gas holdup in different regions are close related. Any suitable differential pressure sensing device which provide a suitable signal output in response to the thus sensed differential pressure can be employed. Preferred sensing devices are those intended for pressure measurements in sanitary applications and features, stainless steel seal diaphragms, and isolated electrodes forming a variable capacitor. Pressure applied to the pressure sensors causes slight deflections of the diaphragms which changes the capacitance. This capacitance is detected and converted to a highly accurate signal, proportional to the sensed differential pressure by a transmitter 24. Output signal from the transmitter 24 is transmitted by a suitable conduit 14 to a control unit 17. Coalescence is strongly impeded during a fermentation process, due to extracellular materials released from microorganisms. Since smaller bubbles are formed and maintained, more air bubbles are entrained into the downflow. As a result, the gas holdup in the gassed broth mixture within the fermentor is increased as a function of time. It is important that gas holdup does not exceed a certain maximum value, as this adversely affects the circulation rate, the bulk mixing and the volume utilization. Differential pressure sensed eventually becomes lower than differential pressure set point, thus indicating a gas holdup in the gassed broth higher than desirable. An output signal 25 from the control unit 17, in response to the sensed differential pressure, provides the actuating signal to adjust the flowrate of antifoam agent delivered to the fermentor, through tubes 23, by the pump 11, from an antifoam container 10.

Many chemical compounds can be used as antifoam agents, these include but are not limited to esters, alcohols, siloxanes, silicones, sulfites, sulfonates, fatty acids and their derivatives. Different control strategies, including proportional, integral, derivative or a combination of them, can be employed to adjust the antifoam agent flow rate in response to the sensed differential pressure. The antifoam agent addition causes an increased rate of coalescence of air bubbles, and consequently a reduction of gas hold up in the gassed broth contained mixture inside the vessel 1. If the gas holdup becomes lower than desired, the antifoam agent flow rate shall be reduced or even stopped through the control action to prevent a further drop of the gas holdup. On the other hand, if the gas holdup becomes higher than desired, the antifoam agent flow rate shall be increased through the control action in order to reduce gradually the gas holdup to the desired values. The controller also can be an on-off type with time delay to prevent overcharging of antifoam. In such a case, if the gas holdup is higher than desired, the antifoam added in response to the control signal 25 will increase the coalescence of the air bubbles, and consequently it will cause a reduction of gas holdup in the vessel 1. If the gas holdup is still higher than the set point after a determined amount of time (for example 3 minutes) from pump 11 activation, a new control action can be allowed. This control action shall be taken as many times as required at predetermined time intervals, while gas holdup remain higher than desired. The amount of antifoam agent added with each control action in this case is very critical, since relatively large amounts of addition, will cause undesirable steep gas holdup reduction and consequently a sharp oxygen transfer rate reduction. Yet, if relatively large quantities of antifoam are added, the gas holdup and the oxygen transfer rate may remain low during a long period of time, and it will take several hours, to enhance them up to desirable values. Optimum amounts of antifoam agent additions depend upon variables such as microorganism, substrate, fermentation conditions, antifoaming type, differential pressure set point among others. Optimum amounts of antifoam agent additions and time span between additions shall be determined in advance in trial runs.

Accumulation of stable foam within the upper portion of the vessel, is effectively prevented by controlling the gassed broth level within a suitable range in the fermentor and by this means providing a broth flow path such that, foam in "statu nacendi" is effectively entrained into the downcomer, through a ring vortex induced on the free surface near the fermentor wall by the broth flow deflection from the draft tube to the annular space. The simplest way to maintain a desired gassed broth level is by providing the vessel 1, with one or more overflow pipes 9, which provide means for drawing off a portion of the broth to maintain the gassed broth level below the line A-A' in FIG. 1. Alternatively, a wide variety of level transmitter instruments can be employed to measure interface between gassed broth and gas phase and provide a suitable signal output for automatically controlling the gassed broth level.

In the fermentor described in the preceding paragraphs, the riser occupies the central region of the fermentor and the downcomer section surround it. It is equally possible and preferred in some cases that the downcomer section should be in the center and the riser should form annuli around it. Many other geometrical arrangements are possible, coaxial and symmetrical arrangements are preferred, however non coaxial and non symmetrical are also possible.

Figure 2:
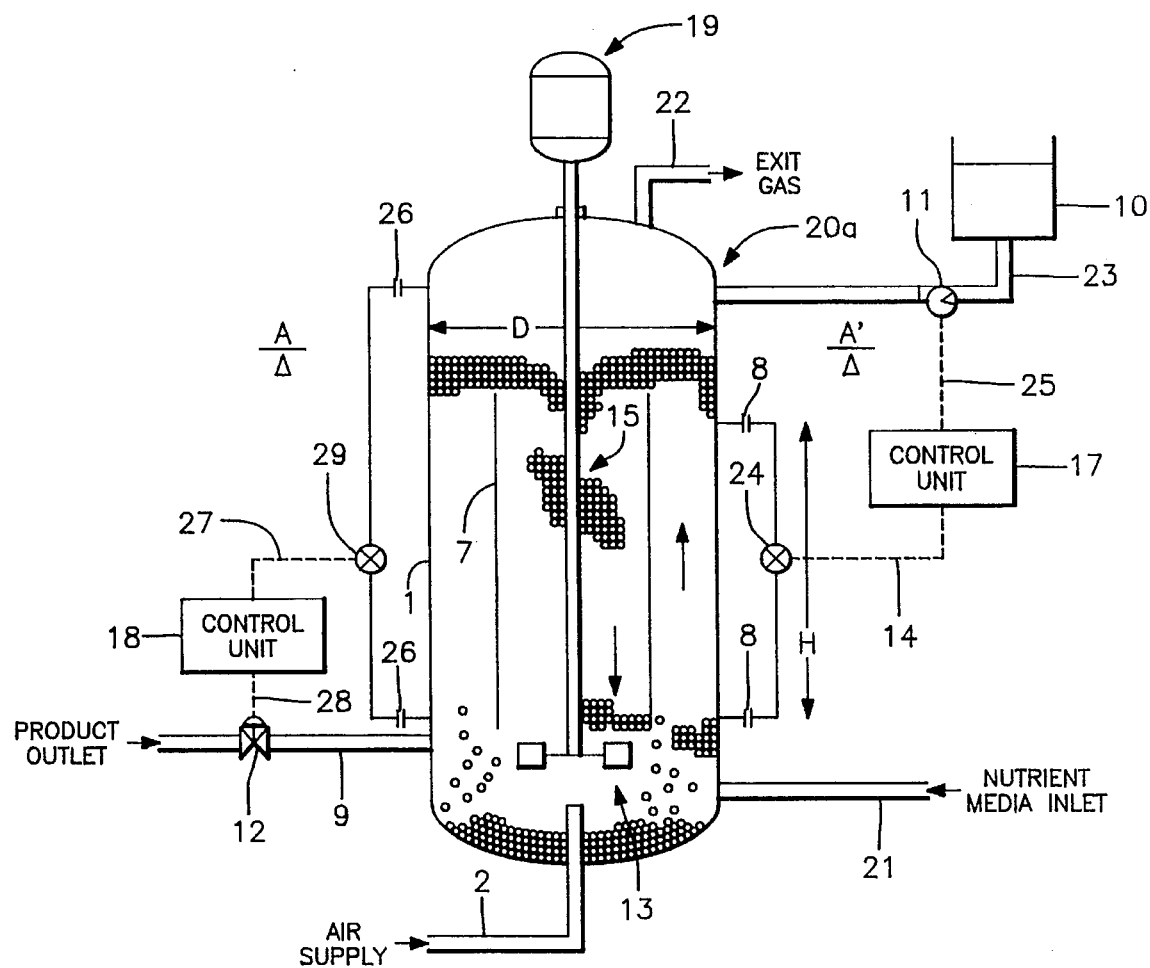
FIG. 2 is a side elevation of a second embodiment of the fermentor according to the invention.

FIG. 2 illustrates another form of fermentation apparatus 20a, which is a modified version of the apparatus 20. The elements of the apparatus 20a having the same function to the previously described apparatus 20, are identified by the same reference numerals. The apparatus 20a differs from the apparatus 20 in the following aspects.

Apparatus 20a is equipped with an agitation system, having a turbine impeller 13, a shaft 15, and a driver 19. In apparatus 20a air dispersion in the broth, is achieved by means of the high shear stress produced by the rotating turbine impeller.

In apparatus 20a, accumulation of foam within the upper end portion of the vessel is prevented by controlling the broth volume in the fermentor and by this means providing a broth flow path such that foam in "statu nacendi" is effectively entrained into the downcomer through a central vortex induced by the broth flow deflection from the annular space to the draft tube. In this case, apparatus 20a is provided with a liquid level control system which under controlled gas holdup conditions, provide means for measurement and control of the gassed broth level. The liquid level control system comprises: a differential pressure sensing device 26, a transmitter 29, a control unit 18, and a suitable valve 12. Differential pressure sensing device 26, has a bottom pressure sensor suitably located to be in contact with the gassed broth, and a top sensor suitably located to be in contact with the gas phase. The control unit 18, provides an actuating signal 28, to adjust the valve 12, which provides means for regulated drawing off of the broth, in response to the differential pressure signal transmitted via conduit 27, to said control unit 18.

In apparatus 20 and 20a above described, hydrodynamic foam suppression is achieved by maintaining a proper gassed broth level and by maintaining a proper broth level respectively. As it is well known, other means can be employed to provide a suitable signal output in response to the gassed broth level or alternatively to the broth level, and provide a suitable signal to control any of these parameters. Suitable means may include but are not restricted to conductive, capacitive, ultrasonic, displacer, and float transmitters.

Various applications for the fermentor and fermentation method of our invention are feasible for both, production of microorganisms to obtain cellular protein or for production of various extracellular and intracellular products by biochemical conversion. A wide variety of carbon sources may be used for example carbohydrates, hydrocarbons, and alcohols. Preferably yeast or bacteria are cultivated at temperatures between 20° to 45° C. under aerobic conditions in the fermentor containing a broth having a pH value of 2.5 to 8. The fermentor 20 is especially useful for conducting a continuous fermentation process wherein a nutrient medium is continuously fed through an inlet 21 to the vessel 1, and a broth containing the desired microbial cells or metabolites is continuously withdrawn via the outlet 9 for further processing (not shown). Such further processing can include recovery of cells from the fermentation effluent by conventional means, such as by centrifugation, filtration or other separation means. The cellular product can be washed to remove unconsumed mineral salts and extracellular products such as amino acids, enzymes, biopolymers and the like. The washed cells can then be dried to produce a dried product.

The washings and the substantially cell free effluent contain the residual mineral salts not incorporated into the cells and extracellular products. These streams can be treated to recover or isolate extracellular products such as enzymes, biopolymers, and others. For instance, a lower alcohol such as methanol or ethanol can be used to precipitate any polymeric material produced extracellularly by the microbial cells. The cell free effluent also can be treated by solvent extraction to recover other extracellular products. Alternatively, the total fermentation effluent can be dried to produce a dried product containing cells, salts, and other water soluble substances.

We claim:

1. An apparatus for contacting a liquid with a gas comprising:

a closed cylindrical vessel having an upper region, a lower region and guiding means, said guiding means providing at least one ascending flow chamber and at least one descending flow chamber, said chambers communicating at said upper and lower regions of said vessel;

a first inlet for introducing a liquid into said vessel;

a second inlet for introducing a gas into said vessel;

means for dispersing said gas into said liquid, in said vessel, forming a gassed liquid;

a liquid outlet for withdrawing said liquid from said vessel to maintain a gassed liquid level above said guiding means in said vessel; such that in use a liquid vortex is induced as a result of liquid flow deflection from said ascending flow chamber to said descending flow chamber, thereby preventing foam formation;

a gas outlet located in the upper region of the vessel above said gassed liquid level;

a gas holdup sensing means at least partially disposed within said vessel for sensing the gas holdup of the gassed liquid in said vessel;

antifoam supply means for delivery of an antifoam agent into said vessel; and control means operatively linked to said gas holdup sensing means and to said antifoam supply means, such that in operation the detected gas holdup is used by said control means so as to regulate the amount of antifoam agent added to said vessel by said antifoam supply means.

2. The apparatus of claim 1 wherein said liquid outlet comprises an overflow pipe located in an upper region of the vessel.

3. The apparatus of claim 1 wherein said liquid outlet is operatively connected to a control means which is operatively connected to a gassed liquid level sensing means, such that in use the sensed gassed liquid level is used by said control means so as to regulate the amount of liquid withdrawing from said vessel through said liquid outlet.

4. The apparatus of claim 3 wherein said gassed liquid level sensing means comprises an interface sensing device for measuring the interface between gassed liquid and gas phase in said upper region of said vessel.

5. The apparatus of claim 1 wherein said liquid outlet is operatively connected to a control means which is operatively connected to a differential pressure sensing device, which measures the level of said liquid in said vessel, such that in use the sensed differential pressure is used by said control means so as to regulate the amount of liquid being withdrawn from said vessel through said liquid outlet.

6. The apparatus of claim 1 wherein said gas holdup sensing means comprises at least one differential pressure sensor.

* * * * *